(12) United States Patent
Kweon et al.

(10) Patent No.: US 10,994,048 B2
(45) Date of Patent: May 4, 2021

(54) METHOD FOR MANUFACTURING HYALURONATE FIBERS BY USING MELT SPINNING AND HYALURONATE FIBERS MANUFACTURED THEREBY

(71) Applicant: JINWOO BIO CO., LTD., Seoul (KR)

(72) Inventors: Dong Keon Kweon, Yongin-si (KR); Seung Hyeon Park, Seoul (KR)

(73) Assignee: JINWOO BIO CO., LTD., Seoul (KR)

( * ) Notice: Subject to any disclaimer, the term of this patent is extended or adjusted under 35 U.S.C. 154(b) by 379 days.

(21) Appl. No.: 15/757,605

(22) PCT Filed: Sep. 1, 2016

(86) PCT No.: PCT/KR2016/009748
§ 371 (c)(1),
(2) Date: Mar. 5, 2018

(87) PCT Pub. No.: WO2017/039335
PCT Pub. Date: Mar. 9, 2017

(65) Prior Publication Data
US 2018/0243471 A1 Aug. 30, 2018

(30) Foreign Application Priority Data

Sep. 3, 2015 (KR) .................. 10-2015-0125088

(51) Int. Cl.
*A61L 27/20* (2006.01)
*D01D 5/08* (2006.01)
(Continued)

(52) U.S. Cl.
CPC .............. *A61L 27/20* (2013.01); *A61B 17/06* (2013.01); *A61K 31/728* (2013.01); *A61L 17/10* (2013.01);
(Continued)

(58) Field of Classification Search
CPC ....... A61B 17/06; D01D 5/08; D10B 2509/04
See application file for complete search history.

(56) References Cited

U.S. PATENT DOCUMENTS 5,616,568 A * 4/1997 Pouyani .............. C08B 37/0072
514/53
2006/0046590 A1 * 3/2006 Chu ..................... C08B 37/0072
442/59
(Continued)

FOREIGN PATENT DOCUMENTS

JP 2007-262595 A 10/2007
JP 2009-041117 A 2/2009
(Continued)

OTHER PUBLICATIONS

Kupska, Ivana—The viscometric behavior of sodium hyaluronate in aqueous and KCL solutions, 2014, Colloids and Surfaces A, pp. 33-37 (Year: 2014).*

(Continued)

*Primary Examiner* — Jacob T Minskey
*Assistant Examiner* — Virak Nguon
(74) *Attorney, Agent, or Firm* — Novick, Kim & Lee, PLLC; Jae Youn Kim

(57) ABSTRACT

Provided is a hyaluronate fiber, and more particularly to a hyaluronate fiber, suitable for use in a surgical suture, a filler for cosmetic surgery, a lifting thread, a tissue-engineering scaffold, etc., and a method of manufacturing the same. Further, a method of manufacturing the hyaluronate fiber through melt spinning is provided, which includes (a) controlling the water content of a hyaluronate having a weight average molecular weight of 500~3,000 kDa to 5~20%, (b) producing a hyaluronate fiber by placing the hyaluronate having a controlled water content in a melt-spinning apparatus and performing heating to 150~200° C. and then (Continued)

high-pressure spinning, and (c) hardening the surface of the hyaluronate fiber by immersing the hyaluronate fiber in an ethanol aqueous solution.

10 Claims, 2 Drawing Sheets

(51) Int. Cl.
    *D01F 9/00*     (2006.01)
    *A61L 27/58*     (2006.01)
    *A61K 31/728*     (2006.01)
    *A61B 17/06*     (2006.01)
    *A61L 17/10*     (2006.01)
    *A61L 27/50*     (2006.01)
    *A61L 27/54*     (2006.01)
    *A61L 31/04*     (2006.01)
    *A61L 31/14*     (2006.01)
    *A61L 31/16*     (2006.01)
    *C08B 37/08*     (2006.01)
    *C08J 5/00*     (2006.01)
    *D01F 11/00*     (2006.01)
(52) U.S. Cl.
    CPC .............. *A61L 27/50* (2013.01); *A61L 27/54* (2013.01); *A61L 27/58* (2013.01); *A61L 31/042* (2013.01); *A61L 31/14* (2013.01); *A61L 31/16* (2013.01); *C08B 37/0072* (2013.01); *C08J 5/00* (2013.01); *D01D 5/08* (2013.01); *D01F 9/00* (2013.01); *D01F 11/00* (2013.01); *A61L 2400/06* (2013.01); *C08J 2305/08* (2013.01); *D10B 2509/04* (2013.01)

(56) References Cited

U.S. PATENT DOCUMENTS

| | | | | |
|---|---|---|---|---|
| 2006/0134158 | A1* | 6/2006 | Majima | ................ A61L 27/20 424/422 |
| 2006/0281912 | A1* | 12/2006 | James | ................ C08B 37/0072 536/53 |
| 2010/0255068 | A1* | 10/2010 | Stroumpoulis | ........ A61K 8/027 424/443 |
| 2010/0310631 | A1* | 12/2010 | Domard | ................ D01D 5/06 424/443 |
| 2012/0021217 | A1 | 1/2012 | Hadba et al. | |
| 2015/0119783 | A1* | 4/2015 | Burgert | ................ C08L 1/286 602/42 |
| 2015/0308016 | A1* | 10/2015 | Scudlova | ............ A61L 31/042 428/221 |
| 2016/0145357 | A1* | 5/2016 | Karlsson | ................ A61Q 19/08 536/53 |

FOREIGN PATENT DOCUMENTS

| | | |
|---|---|---|
| JP | 2011-31034 A | 2/2011 |
| JP | 2012-501391 A | 1/2012 |
| JP | 2014-533992 A | 12/2014 |
| JP | 2015-522720 A | 8/2015 |
| JP | 2016-502612 A | 1/2016 |
| JP | 2016-505722 A | 2/2016 |
| KR | 10-2012-0015655 A | 2/2012 |
| KR | 2012-0015655 A | 2/2012 |
| KR | 10-2014-0006851 A | 1/2014 |
| KR | 2014-0100469 A | 8/2014 |
| WO | 2012089179 A1 | 12/2011 |
| WO | 2013055832 A1 | 10/2012 |
| WO | 2013167098 A2 | 5/2013 |

OTHER PUBLICATIONS

Stanford Chemicals—Medical Grade Sodium Hyaluronate (Year: 2015).*
Min Zhang et al, "Synthesis and properties of melt-processable hyaluronan esters", Journal of Materials Science: Materials in Medicine 16 (2005) p. 587-593.
Li, Study of electrospinning of natural biopolymer, Polymer Chemistry and Physics, Jan. 7, 2003, pp. 1-136.

* cited by examiner

US 10,994,048 B2

METHOD FOR MANUFACTURING HYALURONATE FIBERS BY USING MELT SPINNING AND HYALURONATE FIBERS MANUFACTURED THEREBY

TECHNICAL FIELD

The present invention relates to a hyaluronate fiber, and more particularly to a hyaluronate fiber, suitable for use in a surgical suture, a filler for cosmetic surgery, a lifting thread, a tissue-engineering scaffold, etc., and a method of manufacturing the same.

BACKGROUND ART

Hyaluronic acid (HA) is a colorless high-viscosity polysaccharide having a molecular weight of 500,000 to 13,000,000 Da, and is configured such that D-glucuronic acid and N-acetylglucosamine, which are repeating units, are alternately linked by (1-3) and (1-4) bonds.

HA is involved in a variety of human physiological activities and is known to have various physiological activities depending on the molecular weight thereof. In particular, polymeric HA is used as a space filler, and is known to possess anti-angiogenic and immunosuppressive functions.

Thus, HA of 2.0 MDa or more in the form of a high-viscosity hydrogel is currently widely utilized as an injecting agent for joints, a filler for cosmetic surgery, and an adhesion inhibitor for internal and external surgery. However, most products are in the form of a liquid such as a high-viscosity aqueous solution or hydrogel, and are thus limited in usability, storability and processability. Moreover, upon use in the form of a liquid, the stability of HA itself decreases, and care should be taken to store and distribute the product. The HA content in the actual product is as low as about 1~5%, making it impossible to inject high-concentration HA in a large amount into a human patient, and also, injection pressure due to the high volume thereof leads to great pain for the patient.

Furthermore, when HA is injected in vivo in the form of liquid, it is rapidly degraded by various lyases present in vivo to thus decrease the molecular weight thereof, whereby the persistence in vivo is also lowered and the effect on the treatment site is deteriorated.

With the goal of improving the stability and usability of HA, Korean Patent Application Publication No. 2014-0100469 and Japanese Patent Application Publication No. 2011-31034 disclose a suture in which a safe degradable polymer as a main material is blended or coated with a small amount, specifically 10% or less, of HA, but are problematic because of low HA content.

Although the HA content may be increased upon production of a fiber composed exclusively of HA, a method of manufacturing a fiber composed exclusively of HA has not yet been known because it is impossible to melt HA owing to strong hydrogen bonding in the HA polymer polysaccharide.

Therefore, the present inventors have made efforts to solve the above problems and thus have ascertained that, when non-melting hyaluronate is controlled in the water content thereof through pretreatment and is then melt spun, a sodium hyaluronate fiber, suitable for use in a surgical suture, a filler for cosmetic surgery, a tissue-engineering scaffold, and the like, may be manufactured, thus culminating in the present invention.

DISCLOSURE

Technical Problem

Accordingly, the present invention is intended to provide a hyaluronate fiber and a method of manufacturing the same, in which the hyaluronate fiber is composed mainly of a hyaluronate having excellent biocompatibility, skin elasticity and moisture retention.

In addition, the present invention is intended to provide a surgical suture, a filler for cosmetic surgery, a lifting thread, and a tissue-engineering scaffold, manufactured using the hyaluronate fiber having high safety and biocompatibility.

Technical Solution

Therefore, the present invention provides a method of manufacturing a hyaluronate fiber through melt spinning, comprising the steps of: (a) controlling the water content of a hyaluronate having a weight average molecular weight of 500~3,000 kDa to 5~20%; (b) producing a hyaluronate fiber by placing the hyaluronate having a controlled water content in a melt-spinning apparatus and performing heating to 150~200° C. and then high-pressure spinning; and (c) hardening the surface of the hyaluronate fiber by immersing the hyaluronate fiber in an ethanol aqueous solution.

In the present invention, the hyaluronate has a pH of 6~8.

In the present invention, the step of hardening the surface of the hyaluronate fiber comprises immersion once in the ethanol aqueous solution or immersion two to five times while sequentially increasing the ethanol concentration of the ethanol aqueous solution.

In the present invention, the ethanol aqueous solution has a concentration of 30~99 vol %.

Also, the present invention provides a hyaluronate fiber, manufactured by the above method.

Also, the present invention provides a surgical suture, a filler for cosmetic surgery, a lifting thread, and a tissue-engineering scaffold comprising the above hyaluronate fiber.

Advantageous Effects

According to the present invention, a hyaluronate fiber is manufactured using a hyaluronate as a main component and is thus excellent in safety and biocompatibility, and moreover, causes no microbial contamination, unlike typical liquid hydrogel products, and is easy to handle and use and can thus be utilized as formulations in various forms for tissue restoration.

Also, the hyaluronate fiber of the present invention is a product in solid form, and thus the volume thereof relative to the hyaluronate concentration is very low to thus minimize the pain and discomfort of a patient upon in-vivo injection, thereby maximizing the therapeutic effect.

BEST MODE

The present inventors have ascertained that, when hyaluronate, which is not melted due to strong hydrogen bonding, is subjected to wet treatment, melt spinning thereof becomes possible and a hyaluronate fiber having high hyaluronate content may be manufactured, and the properties of the hyaluronate fiber may be adjusted through surface hardening, thus culminating in the present invention.

In an embodiment of the present invention, an endothermic peak due to the melting of sodium hyaluronate having controlled water content is confirmed through measurement using a differential scanning calorimeter (DSC). Based on the measurement results, water content of sodium hyaluronate is controlled to 5~20%, and then melt spinning is performed at 150~200° C., thus manufacturing a sodium hyaluronate fiber. In order to improve the properties thereof, the sodium hyaluronate fiber is sequentially immersed in each of 50%, 70% and 95% ethanol aqueous solutions to thus harden the surface thereof, thereby yielding a hyaluronate fiber.

Consequently, the manufactured sodium hyaluronate fiber can be found to maintain the properties and shape thereof even when immersed in saline for a long period of time.

Thus, an aspect of the present invention addresses a method of manufacturing a hyaluronate fiber through melt spinning, comprising the steps of: (a) controlling the water content of a hyaluronate having a weight average molecular weight of 500~3,000 kDa to 5~20%; (b) producing a hyaluronate fiber by placing the hyaluronate having a controlled water content in a melt-spinning apparatus and performing heating to 150~200° C. and then high-pressure spinning; and (c) hardening the surface of the hyaluronate fiber by immersing the hyaluronate fiber in an ethanol aqueous solution.

In the present invention, the hyaluronate is configured such that HA is coupled with a salt, and examples thereof may include, but are not limited to, sodium hyaluronate, calcium hyaluronate, potassium hyaluronate, etc.

In order to control the water content of the hyaluronate, any process may be performed without limitation, so long as the water content of the hyaluronate may be controlled. For example, the water content of the hyaluronate may be controlled using a thermo hygrostat.

If the water content of the hyaluronate is less than 5%, it is difficult to perform a spinning process due to a difficulty in melting upon melt spinning under conditions of high temperature and high pressure. On the other hand, if the water content of the hyaluronate exceeds 20%, it is difficult to maintain the shape of the fiber even after the hardening process due to the high water content of the fiber after the spinning process.

Figure 1:
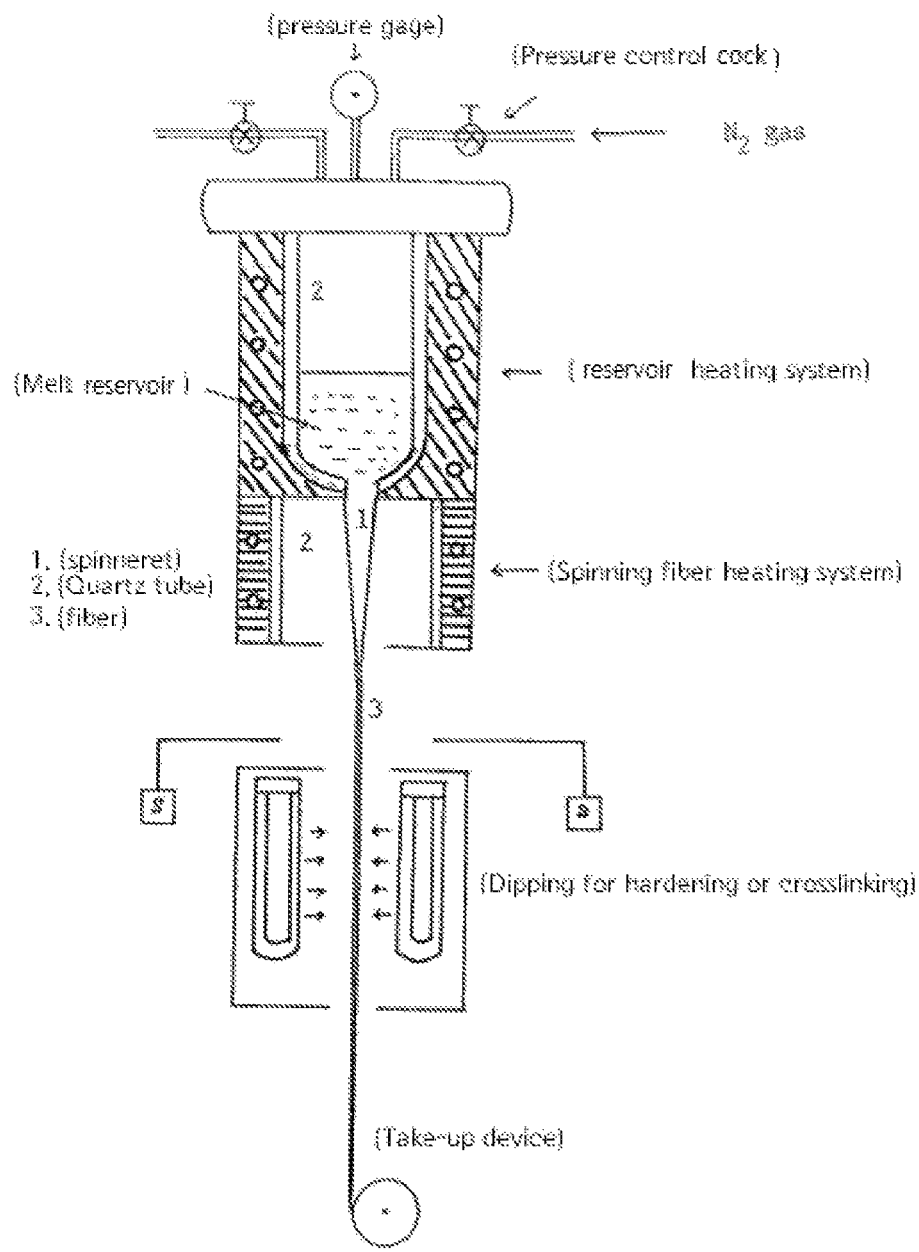
FIG. 1 shows a melt-spinning apparatus used in the present invention.
Figure 2:
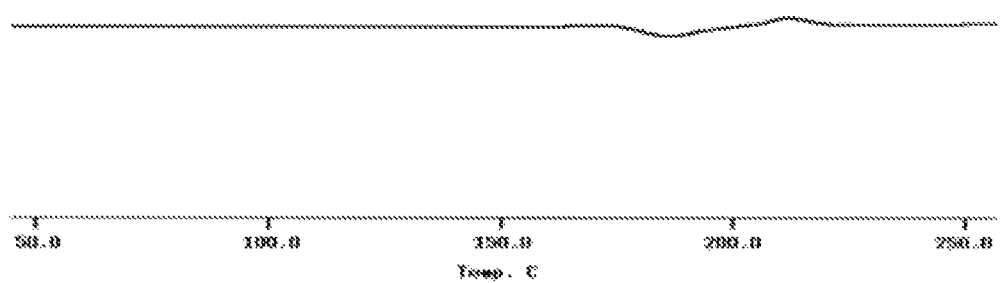
FIG. 2 shows the DSC results before control of the water content of polymeric hyaluronate and after control of the water content thereof to 10%.
Figure 2:
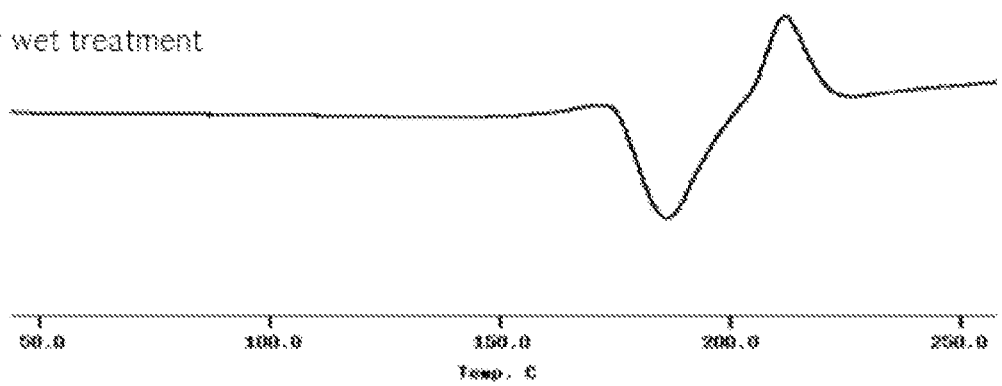

In the present invention, the hyaluronate having a controlled water content of 5~20% is placed in the melt reservoir of a melt-spinning apparatus (FIG. 1), heated to 150~200° C., and spun under high pressure, thus manufacturing a hyaluronate fiber.

Although the hyaluronate fiber according to the present invention may be manufactured using hyaluronate alone, carrier or excipient components, which are typically used in the art, may be further added depending on the field of use thereof, and the kinds and amounts thereof are not particularly limited.

In order to ensure more enhanced properties and functionality upon application as a formulation for tissue restoration, which is the main end use of the present invention, HA may be mixed with a cellulose material, which is a pharmacologically acceptable biocompatible agent, and with a highly degradable polymer, such as polyethylene, polydioxanone, polyvinyl alcohol, polyvinyl ether, polyvinyl pyrrolidone, or polylactic acid, and then spun.

In the case where a hyaluronate fiber, manufactured by subjected a hyaluronate to melt spinning and drying, is used without change, it is difficult to store, and the properties thereof are difficult to maintain owing to the moisture sensitivity of HA itself, undesirably causing problems of stability.

With the goal of solving the above problems, in the present invention, the hyaluronate fiber is immersed in an ethanol aqueous solution, and thus the surface thereof is hardened.

Hardening the surface of the sodium hyaluronate fiber is performed through immersion once (an immersion time of about 1 sec) in a 90~99 vol % ethanol aqueous solution or immersion two to five times (an immersion time of about 1 sec) while sequentially increasing the ethanol concentration of an ethanol aqueous solution.

The concentration of the ethanol aqueous solution that is used for surface hardening treatment is 30~99 vol %, and preferably 50~95 vol %.

Also, in the present invention, a surface crosslinking step may be further conducted in a manner in which the surface-hardened sodium hyaluronate fiber is immersed in an aqueous solution of a crosslinking synthetic chemical, such as glutaraldehyde, epichlorohydrin, etc., or in an aqueous solution of a natural polymer material, which is cationic upon water dissolution, such as chitosan, polylysine, etc. The sodium hyaluronate fiber, a portion of the surface of which is crosslinked, may be improved in degradation resistance and mechanical properties.

Another aspect of the present invention addresses a hyaluronate fiber manufactured by the above method.

The hyaluronate fiber according to the present invention may be manufactured with a hyaluronate purity of 100%, and the surface thereof is firmly hardened or crosslinked, and thus the hyaluronate fiber of the invention has no microbial contamination, unlike existing liquid hyaluronate products for tissue restoration, and is easy to handle and use, and thus may be utilized as formulations in various forms for tissue restoration.

Thus, a further aspect of the present invention addresses a surgical suture, a filler for cosmetic surgery, a lifting thread, and a tissue-engineering scaffold comprising the aforementioned hyaluronate fiber.

MODE FOR INVENTION

A better understanding of the present invention may be obtained through the following examples, which are set forth to illustrate, but are not to be construed as limiting the scope of the present invention, as will be apparent to those skilled in the art.

Example 1: Preparation of HA Paste Through Wet Treatment

Sodium hyaluronate (Hi-Aqua™, made by JinWOO Bio) having a molecular weight of 1.2 MDa was subjected to wet treatment using a thermo hygrostat. Specifically, 10 g of sodium hyaluronate was allowed to stand at a relative humidity of 60% for 1~3 hr, whereby the water content of the sodium hyaluronate was controlled to 5~30%. For reference, the water content of HA before wet treatment was about 2%.

Test Example 1: DSC Measurement

The endothermic peaks of sodium hyaluronate before wet treatment and sodium hyaluronate subjected to wet treatment in Example 1 were measured under conditions of a temperature of 30~250° C. and a heating rate of 10° C./min using a differential scanning calorimeter (DSC6100, Seiko, Japan). Based on the results of DSC measurement, sodium hyaluronate powder not subjected to wet treatment was not detected in an endothermic peak due to melting, whereas sodium hyaluronate, the water content of which was controlled to 5% or more, was strongly detected in an endothermic peak due to melting in the temperature range of about 150~200° C. Accordingly, melt spinning of the sodium hyaluronate can be confirmed to be possible in the above temperature range.

Example 2: Production of HA Fiber Through Melt Spinning

The sodium hyaluronate subjected to wet treatment in Example 1 was placed in the melt reservoir of a melt-spinning apparatus, spun at 150~200° C. under nitrogen pressure, and dried at room temperature in a typical manner, thus manufacturing a sodium hyaluronate fiber (HA fiber).

Example 3: Production of HA Fiber Through Melt Spinning and Surface Hardening A HA fiber, manufactured through spinning in the same manner as in Example 2, was sequentially immersed in 50% ethanol, 70% ethanol, and 95% ethanol to thus harden the surface thereof, followed by typical drying at room temperature, thereby manufacturing a sodium hyaluronate fiber (HA fiber).

Example 4: Production of HA Fiber Through Melt Spinning and Surface Hardening A HA fiber, manufactured through spinning in the same manner as in Example 2, was directly immersed in 95% ethanol to thus harden the surface thereof, followed by typical drying at room temperature, thereby manufacturing a sodium hyaluronate fiber (HA fiber).

Example 5: Production of HA Fiber Through Melt Spinning and Surface Hardening A HA fiber, manufactured through spinning in the same manner as in Example 2, was directly immersed in 50% ethanol to thus harden the surface thereof, followed by typical drying at room temperature, thereby manufacturing a sodium hyaluronate fiber (HA fiber).

Test Example 2: Measurement of Water Swelling Ratio

The sodium hyaluronate fibers (HA fibers) of Examples 2 to 5 were immersed in saline at 37° C., and the swelling rate over time was measured. The results are shown in Table 1 below.

For reference, the swelling rate was determined using the following equation.

Swelling rate (%)=(weight of HA fiber after lapse of a predetermined period of time/initial weight of HA fiber)×100

TABLE 1

| | Swelling ratio (%) | | | | | |
|---|---|---|---|---|---|---|
| | 1 hr | 2 hr | 3 hr | 5 hr | 12 hr | 24 hr |
| Example 2 | 138 | — | — | — | — | — |
| Example 3 | 111 | 118 | 123 | 128 | 135 | 148 |
| Example 4 | 108 | 115 | 119 | 123 | 130 | 141 |
| Example 5 | 125 | 138 | 143 | — | — | — |

As is apparent from Table 1, 2 hr after immersion in saline of the sodium hyaluronate fiber (HA fiber) of Example 2 not subjected to surface hardening, the shape of the fiber was not maintained, making it impossible to measure the swelling ratio.

24 hr after immersion in saline of the sodium hyaluronate fiber (HA fiber) of Example 3, subjected to surface hardening using 30%, 50% and 95% ethanol aqueous solutions, the swelling ratio was about 148%, from which the fiber surface was confirmed to be strongly hardened through hardening treatment to thus maintain the shape of the fiber.

24 hr after immersion in saline of the sodium hyaluronate fiber (HA fiber) of Example 4, subjected to surface hardening using 95% ethanol aqueous solution, the shape of the fiber was maintained. However, 5 hr after immersion in saline of the sodium hyaluronate fiber (HA fiber) of Example 5, subjected to surface hardening using 50% ethanol aqueous solution, it was impossible to maintain the shape of the fiber.

Although specific embodiments of the present invention have been disclosed in detail as described above, it is obvious to those skilled in the art that such description is merely of preferable exemplary embodiments and is not construed to limit the scope of the present invention. Therefore, the substantial scope of the present invention will be defined by the appended claims and equivalents thereof.

INDUSTRIAL APPLICABILITY

The hyaluronate fiber of the present invention can be utilized for a surgical suture, a filler for cosmetic surgery, a tissue-engineering scaffold, etc.

The invention claimed is:

1. A method of manufacturing a hyaluronate fiber through melt spinning, comprising the steps of:
   (a) controlling a water content of a hyaluronate having a weight average molecular weight of 500~3,000 kDa to 5~20%;
   (b) producing the hyaluronate fiber by placing the hyaluronate having the controlled water content in a melt-spinning apparatus and performing heating to 150~200° C. and then pressure spinning; and
   (c) hardening a surface of the hyaluronate fiber by immersing the hyaluronate fiber in an ethanol aqueous solution.

2. The method of claim 1, wherein the hyaluronate has a pH of 6~8.

3. The method of claim 1, wherein the step of hardening the surface of the hyaluronate fiber comprises immersing the hyaluronate fiber once in the ethanol aqueous solution or immersing the hyaluronate fiber two to five times while sequentially increasing an ethanol concentration of the ethanol aqueous solution.

4. The method of claim 1, wherein the ethanol aqueous solution has a concentration of 30~99 vol %.

5. A hyaluronate fiber, comprising solely a hyaluronate having a weight average molecular weight of 500~3,000 kDa.

6. A surgical suture, comprising the hyaluronate fiber of claim 5.

7. A filler for cosmetic surgery, comprising the hyaluronate fiber of claim 5.

8. A lifting thread, comprising the hyaluronate fiber of claim 5.

9. A tissue-engineering scaffold, comprising the hyaluronate fiber of claim 5.

10. A hyaluronate fiber, comprising solely a hyaluronate having a weight average molecular weight of 500~3,000 kDa,
  wherein, when the hyaluronate fiber is immersed in saline at 37° C. for 24 hours, a swelling ratio of the hyaluronate fiber is 141~148%, and a shape of the hyaluronate fiber is maintained, and
  wherein the swelling ratio (%)=(weight of the hyaluronate fiber after lapse of the 24 hour immersion/initial weight of the hyaluronate fiber)×100.

\* \* \* \* \*